United States Patent [19]

Eoga et al.

[11] Patent Number: 5,384,062
[45] Date of Patent: Jan. 24, 1995

[54] PERBORATE PERSULFATE: PROTEASE DENTURE CLEANSER TABLET COMPOSITION

[75] Inventors: Anthony B. Eoga, Boonton; Richard G. Moran, Lake Hopatcong, both of N.J.

[73] Assignee: Warner-Lambert Company, Morris Plains, N.J.

[21] Appl. No.: 160,378

[22] Filed: Dec. 1, 1993

[51] Int. Cl.$^6$ .............. A61K 7/30; C11D 3/39; C11D 3/48; C11D 17/00
[52] U.S. Cl. ..................... 252/99; 252/95; 252/102; 252/106; 252/174; 252/174.12; 252/174.23; 252/527; 252/DIG. 2; 252/DIG. 11; 252/DIG. 12; 252/DIG. 16
[58] Field of Search .............. 252/95, 99, 102, 106, 252/174, 174.12, 174.23, 527

[56] References Cited

U.S. PATENT DOCUMENTS

| | | | |
|---|---|---|---|
| 3,243,377 | 3/1966 | Roy et al. | 252/95 |
| 3,607,759 | 9/1971 | Barth | 252/100 |
| 3,793,211 | 2/1974 | Kohlhepp et al. | 252/99 |
| 3,821,117 | 6/1974 | Breece et al. | 252/99 |
| 3,936,385 | 2/1976 | Cheng | 252/99 |
| 3,962,107 | 6/1976 | Levin | 252/100 |
| 3,997,459 | 12/1976 | Bogie | 252/99 |
| 4,062,793 | 12/1977 | Schodel | 252/99 |
| 4,115,293 | 9/1978 | Schoenholz | 252/102 |
| 4,155,868 | 5/1979 | Kaplan | 252/95 |
| 4,180,467 | 12/1979 | Barth | 252/99 |
| 4,256,599 | 3/1981 | Krisp | 252/99 |
| 4,362,639 | 12/1982 | Eoga | 252/99 |
| 4,405,486 | 9/1983 | Eoga | 252/186.31 |
| 4,459,217 | 7/1984 | Bogie | 252/174.14 |
| 4,490,269 | 12/1984 | Gallopo | 252/94 |
| 4,499,001 | 2/1985 | Eoga | 252/99 |
| 4,518,520 | 5/1985 | Eoga | 252/174.23 |
| 4,540,504 | 9/1985 | Eoga | 252/99 |
| 4,552,679 | 11/1985 | Schobel | 252/90 |
| 4,857,224 | 8/1989 | Eoga | 252/99 |
| 5,015,408 | 5/1991 | Reuss | 252/99 |
| 5,055,305 | 10/1991 | Young | 424/466 |
| 5,118,623 | 6/1992 | Boguslawski | 435/222 |

FOREIGN PATENT DOCUMENTS

| | | | |
|---|---|---|---|
| 1089789 | 11/1980 | Canada | C12D 13/00 |
| 0248936 | 6/1986 | European Pat. Off. | A61K 7/30 |
| 0400858 | 5/1990 | European Pat. Off. | A61K 7/20 |
| 3931129 | 9/1989 | Germany | A61K 7/30 |
| 3934390 | 10/1989 | Germany | A61K 7/30 |
| 1374105 | 12/1970 | United Kingdom | C11D 7/14 |
| 2095694 | 10/1982 | United Kingdom | C11D 7/36 |

OTHER PUBLICATIONS

07/045103, Apr.30, 1987, Anthony B. J. Eoga.

Primary Examiner—Dennis Albrecht
Attorney, Agent, or Firm—Jean B. Barish

[57] ABSTRACT

An anhydrous denture cleansing composition is disclosed comprising anhydrous perborate, a perborate monohydrate, a lubricant and compression aid, a monopersulfate, one or proteolytic enzymes, a sequestering agent, and, optionally, excipients, builders, colors, flavors, and surfactants.

29 Claims, No Drawings

PERBORATE PERSULFATE: PROTEASE DENTURE CLEANSER TABLET COMPOSITION

BACKGROUND OF THE INVENTION

1. Field of the Invention

The invention relates to a denture cleansing composition and a process for making such a composition.

2. Description of the Related Art

Denture cleansing generally is carried out either by brushing dentures with a paste or by soaking dentures overnight in an aqueous cleansing solution. Aqueous denture cleanser solutions are known and generally comprise tablets, granules, or powders that are dissolved in water to form a cleansing bath or cleansing system in water.

One type of denture cleansing tablet (herein "tablet") uses an effervescent system including sodium bicarbonate, citric acid and/or alkaline proteolytic cleaning enzymes, bleaching or oxidizing agents, such as alkali metal and alkaline earth metal, perborates, e.g. anhydrous sodium perborate and sodium perborate monohydrate (herein "perborates"), and monopersulfates. This type of tablet requires a small amount of water in preparation to assure cohesion of the tablet. The tablet may or may not require curing.

A second type of tablet uses cleaning enzymes and anhydrous sodium perborate in combination with sodium perborate monohydrate. There are no persulfates in this type of tablet. This second system does not require added water to assure cohesion of the tablet. Production of the tablet does not require heat curing.

The cleansing systems produced by both of these tablets when dissolved in water have drawbacks. The pH of the aqueous solution in the first system is too low (i.e. too acidic) for fully effective cleaning enzyme activity. In addition, the reaction of the monopersulfate in the tablet with chlorides in the water produces a hypochlorite which inactivates the cleaning enzymes in the tablet, further depressing their efficacy. The hypochlorite also reacts with expensive fragrances in the tablet, depressing their efficacy.

The use in tablets of perborate monohydrates that do not inactivate proteolytic cleaning enzymes either directly or indirectly is known. However, the use of potassium monopersulfate in the form of "OXONE", in the presence perborate monohydrate, in a weight ratio of approximately 3:1 has been shown to result in the formation of a sufficient amount of hypochlorite in water to deactivate alkaline proteolytic cleaning enzymes. U.S. Pat. No. 5,118,623 to George Boguslawski and John W. Shultz of Solvay Enzyme Inc., issued Jun. 2, 1992, discloses that many cleaning enzymes are inactivated in the presence of chlorine and other halogens. A paper by Waku et al, CA 78 (17):107533 p discloses inactivity of enzymes in the presence of as little as 0.2 parts per million free chlorine.

The pH of the aqueous solution in the second system is too high (i.e. too basic). This high pH has a tendency to destroy the fragrance of the cleaning solution. In addition, the pH of the second type of tablet may be too high for optimal activity of the cleaning enzyme.

There have been efforts, with limited success, to develop a tablet in which deactivation of cleaning enzymes and fragrances do not occur in the tablets, while good denture cleaning efficacy is still provided.

U.S. Pat. No. 4,409,118 to Anthony Eoga, issued Oct. 11, 1983, discloses an effervescent cleansing composition in tablet form comprising: (1) a phosphate salt; (2) a silicate salt; and (3) at least one perborate salt. At least part of the perborate salt is in a compacted granulated mixture with a polymeric fluorocarbon.

U.S. Pat. No. 4,857,224, to Anthony Eoga, issued Aug. 15, 1989, discloses an effervescent cleansing composition in tablet form comprising: (1) a pregranulated and compressed mixture of an anhydrous perborate, a perborate monohydrate and a polymeric fluorocarbon compound, and (2) a monopersulfate compound. This composition is useful for forming a tablet from monopersulfates and anhydrous perborates.

SUMMARY OF THE INVENTION

One object of the invention is to provide a denture cleansing tablet with reduced hypochlorite formation, thereby eliminating the problem of deactivation of alkaline proteolytic cleaning enzymes.

A further object of the invention is to provide a denture cleansing tablet capable of dissolving in an aliquot of water to produce a denture cleansing bath having a pH suitable for alkaline proteolytic enzymatic cleaning of dentures.

A further object of the invention is to provide a superior denture cleansing tablet that does not require added water in the composition or curing of the tablet.

A further object of the invention is to provide a denture cleansing tablet that provides an initial fragrance in a solid tablet, provides a burst of fragrance upon dissolution of the tablet in water, and retains a substantial amount of fragrance when the resultant solution is allowed to stand overnight.

A further object of the invention is to provide a denture cleansing tablet capable of removing non-stained plaque, stained plaque, non-stained tartar, stained tartar, and any residue or aftertaste which appears to result from a combination of plaque, stained plaque, tartar and stained tartar.

A further object of the invention is to provide a denture cleansing tablet with cleaning enzymes and fragrances that is compressible at the high speeds necessary for commercial production, yet retains its efficacy and stability.

A further object of the invention is to provide a denture cleansing tablet capable of being compressed to a hardness of at least about 15 SCU.

Additional objects and advantages of the invention will be set forth in part in the description that follows. The objects and advantages of the invention may be realized and attained by means of the examples and combinations described in detail herein and in the appended claims.

These and other objectives are achieved by the present invention, which relates to new denture cleansing compositions and their method of preparation comprising:

(a) a pregranulated compressed mixture of an anhydrous perborate, a perborate monohydrate and a lubricant and compression aid; and
(b) a monopersulfate compound;
(c) non-granulated perborate monohydrate;
(d) an effective amount of a proteolytic cleaning enzyme to disrupt the proteinaceous material in plaque;
(e) an effective amount of sequestering agent such as ethylene diamine tetracetic acid (herein "EDTA") to remove calcium deposits and calculus (also referred to herein as "tartar" deposits). The relative amounts of proteolytic enzyme and sequestering agent is sufficient to be effective to remove stains from both plaque and calculus deposits; and (f) An effervescence-producing composition, wherein the concomitant disruption of proteinaceous material and the sequestering of calcium and calculus deposits results in the removal of calculus and plaque deposits as well as the removal of stained calculus and stained plaque deposits.

DETAILED DESCRIPTION OF THE INVENTION

The present invention relates to improved denture cleansing compositions containing EDTA, anhydrous perborate, perborate monohydrate, polymeric fluorocarbon, and proteolytic cleaning enzymes that has excellent cleaning properties and that can be easily tableted and packaged using high speed equipment. The invention also provides a denture cleansing tablet that exhibits a pronounced tablet fragrance, that provides a burst of fragrance when dissolved in solution, and that provides for an enhanced fragrance retention in solution overnight. The invention also provides a tablet for efficient cleaning of the dentures by brushing. The invention further provides for the removal of residue from dentures after simple rinsing of the dentures under warm water.

The inventive composition is unique in solving some of the fragrance and cleaning problems associated with the inclusion of enzymes in denture cleansing tablets. The new inventive composition provides cleaning efficacy and fast dissolution as required of tablet cleansers. In addition, the components of this denture cleanser react less with the fragrance additives than the components of other denture cleansers. Therefore, less fragrance additives are needed to produce the desired fragrance effect, thereby lowering cost. Additionally, the tablets formed from these new compositions exhibit a strong fragrance. The solution formed from the tablets provides an initial burst of fragrance, and the solution retains a substantial amount of fragrance when used for soaking dentures overnight. The anhydrous perborate is preferably an alkali metal perborate or an alkaline earth metal perborate. The amount of anhydrous perborate in the composition can be between about 5% and 25% by weight of the composition. The amount of perborate monohydrate in the composition can be between about 30% to about 45% by weight of the composition.

The weight ratio of anhydrous perborate to perborate monohydrate in the composition is from about 1:3 to about 1:1. The preferred perborate monohydrate is a non-compacted sodium perborate monohydrate in the form of a predried product containing about 0.3% to about 1.5% by weight of water, and preferably less than about 0.2% to about 0.3% by weight of water.

The invention also comprises lubricant and compression aids. Lubricant and compression aids insure good release of the tablet from the tablet die and are well known in the art. Sodium lauryl sulfate, sodium benzoate, polyethylene glycol, talc, metal stearates and polymeric fluorocarbons are all known and acceptable lubricant and compression aids. Although it is insoluble, polytetrafluoroethylene (herein "PTFE") is the preferred lubricant and compression aids. The lubricant and compression aid comprises from about 0.1 to about 0.8% by weight of the pregranulation mixture of anhydrous perborate, sodium perborate monohydrate, and polymeric fluorocarbon. Where a high degree of initial solution clarity is needed, the PTFE may be present in the amounts from about 0.1% to about 0.8%, and more preferably from about 0.6% to about 0.7% PTFE by weight of the composition.

The monopersulfate compound used in the composition is preferably an alkali metal monopersulfate or an alkaline earth metal monopersulfate. A preferred salt is potassium monopersulfate, especially when present in the form of a triple salt compound with potassium bisulfate and potassium sulfate, e.g. $KHSO_5 \cdot KHSO_4 \cdot K_2SO_4$. This triple potassium salt is available commercially from E. I. dupont DeNemours & Co., Inc. and is sold in the mole ratio 2:1:1 under the trademark "OXONE."

The "OXONE" used in the composition is from about 15% to about 27% by weight of the total composition, preferably from about 18% to about 23%, and most preferably from about 20% to about 21%.

The proteolytic cleaning enzyme for removing proteinaceous material or plaque, and calculus or tartar deposits on dentures is preferably a protease such as "ESPERASE". A number of other known proteases that are particularly active in the DH range of from about 9 to about 10.5 are also acceptable. The enzymes that are active in the range of from about 9.3 to about 9.9 are preferred. The enzymes that are active in the range of from about 9.5 to about 9.7 are most preferred. The enzyme may be present in amounts of about 0.2% to about 5% by weight of the composition. Preferably the enzyme comprises about 0.4% to about 3.8% by weight of the composition. Most preferably the enzyme comprises about 1.7% to about 2.8% by weight of the composition. The enzyme should have an activity of 12 KNPU/gram plus or minus about 20%.

Examples of suitable commercially available proteases include "ALCALASE", "SAVINASE", "ESPERASE" (an alkalophilic variant of *Bacillus licheniformis*), all commercially available from Novo-Nordisk Industries A/S; "MEXATASE" and "MAXACAL" from Gift-Brocades, "KUZUSASE" of Showa Denko; and "BPN" protease from *Bacillus subtilus*, made by Genincor or Sigma. The activity of the proteolytic enzyme included in the composition typically ranges from about 0.1–150 AU/g or its equivalent. Mixtures of different proteolytic enzymes may also be used.

Standard measures of enzyme activity include the Anson Unit (AU), the Kilo Novo Protease Unit (KNPU), and the Glycine Unit (GU). These measures of enzyme activity are well known and defined as follows:

One Anson Unit is the amount of enzyme that digests hemoglobin at an initial rate such that there is liberated per minute an amount of TCA-soluble product which gives the same color with phenol reagent as one milliequivalent of tyrosine. The reaction conditions for this measure are given in NIAS method AF4/5-GB, Modified Anson-Hemoglobin Method for the Determination of Proteolytic Activity.

One Glycine Unit is the amount of enzyme that produces the equivalent of one micromole of glycine per minute under assay conditions.

One Kilo Novo Protease Unit (KNPU) is the amount of enzyme that hydrolyses casein at such a rate that the initial rate of formation of peptide/minute corresponds to 1 mole of glycine/minute. The standard conditions for carrying out this test are given in NIAS method AF 162/3-6B Manual DMC (dimethyl casein) Method for the Determination of Proteolytic Activity. The proteolytic enzyme of the invention should have an activity of 12 KNPU/gram plus or minus about 20%.

Sequestering agents are added to the tablet to maintain clarity and to promote calculus, or tartar, removal. Preferred sequestering agents include ethylene diamine tetraacetic acid ("EDTA") and its corresponding alkali salts, as well as other polyfunctional organic acids, such as citric acid, maleic acid, fumaric acid and their corresponding salts. The EDTA may be present in amounts of about 1% to 25% by weight of the composition, preferably about 17% to about 23% by weight of the composition, and most preferably about 19% to 21% by weight of the composition.

The EDTA is preferably present as $Na_4EDTA.2H_2O$, and is preferably dried to a chelating value of 248 or more such that the chelating value is at a sufficient level to compensate for the water which is present in the composition. The EDTA is milled to a U.S.S mesh size profile of:

0% on U.S.S. 20 Mesh
Maximum of 40% on U.S.S. 40 Mesh
Minimum of 75% on U.S.S. 100 Mesh
Maximum of 25% through U.S.S. 100 Mesh The use of EDTA with a mesh-size profile of greater than 25% through U.S.S. 100 mesh results in the preparation of a table with reduced hardness.

Without intending to be bound by theory, it is believed that the sequestering agent functions in the solution of the invention by reacting with the calcium present in the calculus that accumulates on dentures during the day. This reaction renders underlying proteinaceous material, i.e., plaque, on the dentures susceptible to attack by a proteolytic enzyme also present in the solution. The enzyme in turn attacks this plaque, thereby exposing more calculus to attack by the sequestering agent. Any stain attached to the above deposits are also removed in the process.

This synergistic combination of enzyme and sequestering agent in a tablet allows for a more complete removal of both plaque and calculus on dentures. Adsorbed stains, especially those due to accumulated calculus, that had been beyond the reach of single cleansing ingredients are also susceptible to removal by the tablet of this invention.

Free halogens, especially chlorine, typically found in tap water and other raw materials, can inactivate proteolytic cleaning enzymes in a system that also includes perborate and monopersulfate. This invention overcomes this problem by using a weight ratio of from about 3:1 to about 1:1, more preferably about 1.7:1, of perborate monohydrate to "OXONE". This ratio reduces the formation of hypochlorite and free chlorine. In a system with this perborate/persulfate ratio, proteolytic cleaning enzymes are not inactivated and are more available for use in synergistic combination with the sequestering agents to remove plaque and calculus deposits, and stained plaque and stained calculus deposits.

Colorants and fragrances may also be used with the composition of this invention. F.D. & C. and D. & C. dyes and lakes and natural colors may be used. The materials acceptable for the foregoing spectrum of use are preferably water soluble, but they may include water insoluble dye materials found in the Kirk-Othmer Encyclopedia of Chemical Technology, Volume #5, pages 857–884, which text is hereby incorporated herein by reference.

The fragrance is preferably spray dried and prepared to a free moisture content of less than about 5.0% and preferably less than about 3.0%.

The fragrances can be any known free flavor or fragrance oil. For example, one fragrance can be selected from the group consisting of thymol, eucalyptol, methyl salicylate, menthol, peppermint oil and spearmint oil.

In addition to the ingredients set forth above, the present compositions may contain a variety of additional ingredients selected on the basis of desired end use. Thus, for example, the compositions may include detergent compounds, such as organic and inorganic detergents, including non-ionic detergents such as the various polyoxyehtylene ethers of aromatic and aliphatic alcohols, as well as the polyoxyethylene ethers of hydrophobic propylene oxide polymers. Additionally, ethoxylated acids, and amines are also contemplated. The amount of the detergent is preferably about 0.4% to about 5% by weight, and more preferably about 0.5% to 3% by weight, and most preferably 0.5% to 2.0% by weight of the total cleansing composition. The limiting factor for amounts of detergent is that higher quantities prevent dissolution of the tablet and therefore reduce the effective cleaning time. These compounds assist in maintaining a foaming action in the instance where the cleansing compositions are placed in aqueous solution.

One preferred embodiment of the invention is a water soluble effervescent denture cleanser composition, which comprises the novel steps of: (a) preparing an anhydrous perborate, perborate monohydrate and polymeric fluorocarbon compound as a first premix; (b) forming a precompressed pregranulation or plurality of particles therefrom such that the particles are of a size which will promote cohesion of the final tablet; and (c) combining this premix with the other components as described in Examples 1–7, hereinbelow.

In this preferred embodiment of the inventory, the other components of the tablet are dried to a free surface moisture content of from about 0.02% to about 2% by weight of the composition.

Tablets made from the composition of the invention exhibit excellent hardness, on the average of at least about 12 SCU, preferably from about 18 SCU to about 20 SCU. The tablets have demonstrated even higher hardness levels, which allows the manufacturer to choose an appropriate hardness level that will permit disintegration in water at an appropriate rate.

The materials must be in the proper range of mesh size, otherwise tablets produced from the materials may be defective, and exhibit "capping" during the compression stage. In addition, if particles are too large the tablets may not dissolve fast enough. The particle size especially affects the dissolution of EDTA. Particle size also affects the hardness of the tablet.

When added to water the tablets produce a blue colored cleansing bath. This blue color fades after about 3–10 minutes. The rate of fading depends upon the ratio of the persulfate to the perborate, the water bath temperature, and the amount of water used for the bath.

Tablets dissolved in water form a cleansing solution that removes plaque, stain and tartar deposits from dentures. The amount of plaque, stain, and tarter deposits removed is dependant upon the amount of time the denture is soaked in the cleansing solution. Rinsing the dentures after soaking will aid in removing the residual denture cleanser solution and additional plaque, stain, and tartar. It is believed that rinsing may also reduce the "slippery" or "slimy" feeling or the "metallic aftertaste" often associated with dentures immediately following the cleaning process with commercial denture cleansers.

A further understanding of the present invention will be gained from the following illustrative examples.

EXAMPLE 1-7

Methods of preparation

The compositions set forth in Examples 1-7 were prepared as follows. The amounts of each ingredient in the composition are set forth in Table 1.

Example 1 was prepared as follows: A pregranulation mix, or premix, was prepared containing anhydrous sodium perborate, sodium perborate monohydrate, and a small amount of PTFE. The three premix ingredients were combined in a ratio of 14.7/23.9/0.15. All of the anhydrous perborate was used in the premix. The amounts of perborate monohydrate and PTFE in the premix reflect the aforesaid ratio. These three components were blended in a Day blender for about 3 minutes and passed through a chilsonating compacting machine, Model DMC Fitzpatrick, under the following conditions: The chilsonator was set at an air pressure of from about 88 to about 90 psi, and oil pressure of from about 2300 to about 2400 psi, and the roller at high speed using 2-3 amps. The compacted material was then passed through a Model 197S comil having a 0.175 inch spacer, with a 0.032 inch screen at 4200 RPM. The compacted anhydrous perborate, perborate monohydrate and PTFE, hereinafter known as the premix, typically had a U.S.S. Mesh distribution of:

14% on a size 40 mesh screen,
22% on a size 60 mesh screen,
15% on a size 80 mesh screen,
16% on a size 100 mesh screen,
33% through a 100 mesh screen.

The premix had an untapped density of 0.58 grams/ml and a tapped density (100 taps) of 0.79 grams/ml.

The premix as prepared is used in the formulation at approximately 7% by weight.

In a suitable Day blender container set at 50 RPM the following ingredients were combined in sequence in evenly spaced intervals: sodium bicarbonate; dyes and water; sodium tripolyphosphate; sodium carbonate; citric acid; EDTA; "OXONE"; the remainder of the unpregranulated sodium perborate monohydrate; the premix; flavor preblend; sodium saccharin; spray dried fragrance; sodium sulfate; lathanol; sodium benzoate. The remainder of the PTFE was then added and mixed for an additional 3 minutes. The resultant mixture was compressed into a tablet having a diameter of from 27/32" to 15/16", a thickness of approximately 0.190" to 0.151", and a minimum hardness of 12 SCU.

For examples 2-7, a premix was prepared containing anhydrous sodium perborate, sodium perborate monohydrate, and PTFE in the ratio of 45.26/54.18/0.56. All of the anhydrous perborate was used in the premix. The amounts of perborate monohydrate and PTFE in the premix reflect the aforesaid ratio. These three components were blended in a Day blender for about 3 minutes and passed through a chilsonating compacting machine, Model DMC Fitzpatrick, under the following conditions: The chilsonator was set at an air pressure of 89 psi, the oil pressure was set at 2350 psi and the roller at high speed using 2-3 amps. The compacted material was then passed through a Model 1972 comil having 0.175 inch spacer, with a 0.032 inch screen at 4200 RPM. The compacted anhydrous perborate, perborate monohydrate and PTFE, hereinafter known as the premix, typically had a U.S. S. Mesh size distribution of:

14% on a size 40 mesh screen,
25% on a size 60 mesh screen,
11% on a size 80 mesh screen,
15% on a size 100 mesh screen,
35% through a 100 mesh screen.

The premix had an untapped density of 0.58 grams/ml and a tapped density (100 taps) of 0.76 grams/ml.

For best results, the moisture content of the sodium perborate monohydrate should be less than 1.0%. The premix as prepared is used in the formulation at approximately 25% by weight.

After the premix was prepared, the preparation of Examples 2, 5, 6, and 7 was completed as follows: In a suitable Day Blender set at 50 RPM the following ingredients were added in sequence at approximately 90 second intervals; the remainder of the non-pregranulated sodium perborate monohydrate that was not used to prepare the premix; EDTA; potassium monopersulfate; the premix; sodium tripolyphosphate; a preblend of the dyes and sodium bicarbonate and sodium sulfate; solid fragrance; liquid fragrance; and "ESPERASE". The mixture was mixed until the materials were evenly dispersed up to a maximum of 26 minutes. The remainder of the PTFE not used in the premix was then added. The mixture was mixed for one additional minute. Detergent was then added to the mixture and the mixture was mixed up to a maximum of 3 additional minutes. Total maximum mixing time was 30 minutes. The resultant mixture was compressed into a tablet having a diameter of from ¾" to 15/16", a thickness of 0.16", and a minimum hardness of 12 SCU.

The preparation of Examples 3 and 4 was completed in the same manner as Examples 2, 5, 6, and 7, except than EDTA was not added in Example 3, and "ESPERASE" was non added in Example 4. (See Table 1).

The compositions of the tablets prepared according to
Examples 1-7 are set forth in Table 1.

TABLE 1

| Example | Tablet Composition | | | | | | |
|---|---|---|---|---|---|---|---|
| | 1 | 2 | 3 | 4 | 5 | 6 | 7 |
| Sodium Perborate Monohydrate | 387 | 908.0 | 908.0 | 908.0 | 908.0 | 554.4 | 908.0 |
| Sodium Perborate Anhydrous | 83.0 | 365.0 | 365.0 | 365.0 | 365.0 | 223.1 | 365.0 |
| $Na_4EDTA \cdot 2H_2O$ | 119.0 | 540.0 | — | 540.0 | 540.0 | 329.4 | 540.0 |
| "OXONE" (Potassium Mono Persulfate) | 1221.0 | 552.0 | 552.0 | 552.0 | 552.0 | 336.7 | 552.0 |
| Sodium Saccharin | 7.0 | 7.0 | 7.0 | 7.0 | 7.0 | 7.0 | 7.0 |
| "LATHONOL" | 20.0 | 17.2 | 17.2 | 17.2 | 17.2 | 17.2 | 17.2 |

TABLE 1-continued

| Example | Tablet Composition | | | | | | |
|---|---|---|---|---|---|---|---|
| | 1 | 2 | 3 | 4 | 5 | 6 | 7 |
| PTFE | 3.0 | 19.0 | 19.0 | 19.0 | 19.0 | 11.6 | 19.0 |
| "ESPERASE" 12 knpu/gm | — | 40.0 | 40.0 | — | 40.0 | 24.4 | 44.0 |
| Fragrance (Spray Dried) Spearmint Type | 30.0 | 45.0 | 45.0 | 45.0 | 30.0 | 45.0 | — |
| Mixed Fragrances (Spray Dried) (Listerine Essential Oils) | — | — | — | — | — | — | 45.0 |
| Fragrance (Liquid) (Spearmint) | — | — | — | — | 5.4 | — | — |
| Color | 5.1 | 5.05 | 5.05 | 5.05 | 5.05 | 3.1 | 5.05 |
| Sodium Tripoly-Phosphate | 318.0 | 74.3 | 74.3 | 74.3 | 74.3 | 45.2 | 74.3 |
| Na2CO3 | 285.0 | — | — | — | — | — | — |
| Sodium Sulfate | 150.0 | 67.5 | 67.5 | 67.5 | 67.5 | 41.2 | 67.5 |
| Citric Acid | 119.0 | — | — | — | — | — | — |
| NaHCO3 | 342.0 | 25.0 | 25.0 | 25.0 | 25.0 | 15.3 | 25.0 |
| Sodium Benzoate | 20.0 | — | — | — | — | — | — |
| water | 10.0 | — | — | — | — | — | — |
| Total Weight (grams per 1000 tablets) | 3129.0 | 2665.1 | 2125.1 | 2625.1 | 2655.5 | 1653.5 | 2665.1 |

Example 1 is a comparative prior art example of a known composition showing a composition having a higher weight percent of monopersulfate and a lower perborate monohydrate weight percent compared to the inventive compositions.

Example 2, 5, 6 and 7 comprise examples of the invention. Example 2 has both cleaning enzymes and high levels of EDTA. Example 5 is the inventive composition with reduced spray dried fragrance and added liquid fragrance. Example 6 is a reduced weight formulation of Example 2 with the same levels of detergent and fragrance. Example 7 is the inventive formulation composition wherein the spray dried fragrances used are the essential oils used in LISTERINE® antiseptic mouth rinse in the ratio of 1.00/1.50/2.17/1.41 for menthol, thymol, eucalyptol and methyl salicylate respectively at a 20% load based on weight. Example 3 is the same formulation as Example 2 without Na4EDTA.2-H2O. Example 4 is the same formulation as Example 2 without "ESPERASE".

EXAMPLE 8

Stain and Plaque Removal

Tablets were tested for their cleaning ability on tiles that had been coated with a combination of plaque and various food stains of coffee, tea, blueberry and grape juice.

Sets of plaque-coated and food-stained denture tiles were prepared as follows:

Step I: The denture tiles were immersed in a solution containing human saliva and a growth medium. Plaque was allowed to accumulate over 16 hours at 37° C.

Step II: The tiles were removed from the saliva medium and allowed to air dry for a minimum of two hours.

Step III: The plaque coated tiles were then immersed in a solution of coffee, tea, blueberry, and grape juice for 16 hours at room temperature.

Step IV: Step I, II, and III were repeated two additional times. Separate sets of plaque-coated and food-stained tiles (5 tiles in each set) were immersed in beakers containing 125 ml of water at 45° C. Tablets of the compositions of Examples 1–7 were added to separate beakers. At the end of 15 minutes, the treated tiles were dunked in a 200 ml volume of tap water 20 times and the rinsing repeated again with 200 ml of tap water. The tiles were allowed to air dry at room temperature. The tiles were then examined for stain removal and rank ordered for amount of stain removed.

The rank ordering of the tiles, from most stain removal to least stain removal, was as follows:

Example 2, Example 5, and Example 7
Example 6
Example 3
Two tablets Example 1
One tablet Example 1
Example 4
Water These results indicate that there is a synergistic effect between EDTA and "ESPERASE" as demonstrated by the superior stain removal of Examples 2, 5, and 7. Example 6 contained reduced amounts of EDTA and "ESPERASE", yet was also more effective than Example 3, which lacks EDTA, and Example 4, which lacks "ESPERASE".

EXAMPLE 9

Plaque Removal

Sets of plaque-coated denture tiles were prepared as follows:

Step I: The denture tiles were immersed in a solution containing human saliva and a growth medium. Plaque was allowed to accumulate over 16 hours at 37° C.

Step II: The tiles were then removed from the saliva medium and allowed to air dry at room temperature for at least one day.

Separate sets of tiles were immersed in beakers containing 125 ml of water at 45° C. Tablets of the compositions of Examples 1–7 were added to separate beakers. At the end of 15 minutes the treated tiles were rinsed by being dunked in a 200 ml volume of tap water 20 times. The rinsing was repeated again with 200 ml of tap water and the tiles were allowed to air dry at room temperature. The tiles were then stained to highlight the presence of plaque, and were visually inspected. The tiles were rank ordered for amount of plaque removed.

The rank-ordering of the tiles, from most plaque removal to least plaque removal was as follows:
Example 2, Example 5, and Example 7
Example 6
All of the following Examples removed the same amount of plaque:
Example 1
Example 3
Example 4
Water Control These results show the synergy between proteolytic cleaning enzyme and EDTA in Examples 2, 5, 6, and 7. Examples 3 and 4, which do not contain the combination of enzymes and EDTA, exhibited more remaining plaque after treatment than Examples 2, 5, 6, and 7, all of which contain both EDTA and "ESPERASE". Soaking tiles in the inventive compositions followed by rinsing aids in removal of the plaque and tartar and the "slimy" or "slippery" feeling often associated with freshly cleaned dentures.

EXAMPLE 10

Tartar Removal

Sets of tartar and plaque-coated denture tiles were prepared as follows:

Step I: A set of denture tiles were allowed to rotate through a medium of 70 ml of human saliva containing 0.1% of added Calcium Phosphate, Monobasic, and adjusted to a pH of 7.

Step II: The tiles were rotated through a solution for four 24-hour periods using a fresh calcium/saliva solution for each 24-hour immersion period.

Step III: The tiles were air dried at room temperature prior to use for at least two hours.

These tiles were immersed in separate beakers containing 125 ml of water at 45° C. Tablets of the compositions of Examples 1–7 were added to separate beakers. After 15 minutes, the tiles were dunked in 200 ml of tap water 20 times, and the rinsing was repeated again with another 200 ml of tap water. The tiles were then allowed to air dry at room temperature. The tiles were then subjected to a solution of coffee, tea, blueberry and grape as a disclosant and inspected for the presence of tartar. The tablets were rank ordered for amount of tartar removed.

The rank-ordering of the tiles, from most tartar removal to least tartar removal was as follows:
Example 2, Example 5, and Example 7
Example 6
Example 4
Example 3
Two tablets of Example 1
Water control These results also demonstrate the synergistic effect found in inventive Examples 2, 5, 6, and 7. Both Example 3 and 4 exhibit less tartar removal than Examples 2, 5, 6, and 7.

EXAMPLE 11

Fragrance Levels

In order to compare the fragrance levels of the compositions, the tablet of Example 1 was compared to the tablets of Examples 2, 3, 4, 5, and 6 for dry tablet odor. The physical results are set forth in Table 2 below demonstrate the uniformity of the inventive compositions. The inventive compositions exhibited a pronounced fragrance level in the dry tablet.

Example 1 was compared to Examples 2, 3, 4, 5 and 6 for solution fragrance evolution by placing one tablet of each example in 120 ml of water at 45° C. and smelling the burst of fragrance. The compositions prepared according to the invention (Examples 2, 5, 6 and 7) all exhibited an enhanced burst of fragrance in solution. When the solutions were allowed to stand for one hour at room temperature, the inventive compositions all exhibited a pronounced fragrance level, whereas the comparative prior art Example 1 exhibited a chlorine like odor. When the solutions were allowed to continue to stand overnight (16 Hours) the inventive compositions of Examples 2, 5, 6, all exhibited an enhanced fragrance retention level, whereas the prior art formulation Example 1 continued to exhibit a chlorine-like odor. This enhanced fragrance level is believed to be due to the lower amounts of hypochlorite in the inventive composition. This feature allows for the use of lower amount of fragrance in the composition and helps to solve problems associated with stability of some fragrances.

In addition, a tablet from Example 7 was compared to a variation of Example 1, wherein Example 1 contained 70 mg/tablet of the spray dried essential oil fragrance from oils used in LISTERINE ® antiseptic mouth rinse in place of the spearmint spray dried fragrance. The results indicated that the tablet from Example 7 exhibited a much stronger burst of fragrance when the tablet was placed in solution and a stronger fragrance level overnight even though the comparative Example 1 tablet contained 60% more fragrance.

TABLE 2

| Example | | | Fragrance | | | | |
|---|---|---|---|---|---|---|---|
| | 1 | 2 | 3 | 4 | 5 | 6 | 7 |
| pH | 8.3 | 9.65 | 9.60 | 9.65 | 9.65 | 9.60 | 9.60 |
| Fade Time (Min.) | 12 | 7 | 1 | 5 | 6 | 6 | 6 |
| Bomb Value | 14 | 4 | 2 | 4 | 4 | 3 | 10 |
| Theoretical Active Oxygen (mg.) | 115 | 170.2 | 170.2 | 170.2 | 170.2 | 103.9 | 170.2 |
| Actual Active Oxygen (mg.) | 114.0 | 165.7 | 165.7 | 165.7 | 165.7 | 102.1 | 165.7 |
| Disintegration Time (seconds) | 180 | 90 | 90 | 50 | 40 | 90 | 90 |
| Density (100 Taps) | N/A | 1.07 | N/A | N/A | N/A | 0.95 | N/A |
| Thickness (inch) | 0.190 | 0.160 | — | — | 0.160 | 0.160 | 0.160 |
| Diameter | 57/64 | 15/16 | N/A | N/A | 15/16 | 3/4 | 15/16 |

TABLE 2-continued

| | Fragrance | | | | | | |
|---|---|---|---|---|---|---|---|
| Example | 1 | 2 | 3 | 4 | 5 | 6 | 7 |
| (inch) | | | | | | | |

The purpose of the above Examples is to illustrate some embodiments of the present invention without implying limitations. It will be apparent to those skilled in the art that various modifications and variations may be made in the apparatus or procedure of the invention without departing from the scope or spirit of the invention.

We claim:

1. A denture cleansing composition in tablet form derived from a mixture comprising:
   (a) a pregranulated compressed mixture of an anhydrous perborate in an amount of from about 5% to about 25% by weight of said composition, a perborate monohydrate, and a lubricant and compression aid, wherein the weight ratio of anhydrous perborate to said perborate monohydrate in said pregranulated mixture is from about 1.3 to about 1:1, the amount of perborate monohydrate in the premixture being reflected by the ratio; and
   (b) a monopersulfate compound in an amount of from about 15% to about 27% by weight of said composition; and
   (c) non-granulated perborate monohydrate wherein the total amount of granulated and non-granulated perborate monohydrate is in an amount of from about 30% to about 45% by weight of said denture cleansing composition; and
   (d) an effective amount of one or more proteolytic enzyme(s) to disrupt the proteinaceous material in plaque; and
   (e) an effective amount of a sequestering agent to remove calcium deposits and calculus deposits.

2. The denture cleansing composition of claim 1 wherein;
   said anhydrous perborate is potassium or sodium anhydrous perborate;
   (ii) said lubricant and compression aid is in an amount of from about 0.1% to about 0.8% by weight of said pregranulated compressed mixture, and wherein said lubricant and compression aid is polytetrafluorethylene;
   (iii) said monopersulfate compound is a triple potassium salt with the formula $KHSO_5 \cdot KHSO_4 \cdot K_2SO_4$ and a mole ratio of 2:1:1,
   (iv) said proteolytic enzyme is in an amount of from about 0.2% to about 5% by weight of said composition, and wherein said proteolytic enzyme is a protease derived from a variant of Bacillus licheniformis;
   (v) said sequestering agent is in an amount of from about 1% to about 25% by weight of said composition, and wherein said sequestering agent is $Na_4EDTA \cdot 2H_2O$.

3. The composition of claim 1, wherein said anhydrous perborate comprises about 13% to about 14% by weight of said composition.

4. The composition of claim 1, wherein said perborate monohydrate comprises about 33% to about 35% by weight of the total cleansing composition.

5. The composition of claim 1 wherein said lubricant and compression aid is polytetrafluourethylene.

6. The composition of claim 1, wherein said lubricant and compression aid comprises from about 0.1% to about 0.8% by weight of the pregranulated compressed mixture.

7. The composition of claim 1 wherein said monopersulfate compound is a triple potassium salt with the formula $KHSO_5 \cdot KHSO_4 \cdot K_2SO_4$ and a mole ratio of 2:1:1.

8. The composition of claim 7, wherein said monopersulfate compound comprises from about 15% to about 27% by weight of said composition.

9. The composition of claim 1, wherein said sequestering agent is EDTA.

10. The composition of claim 9, wherein said EDTA is $Na_4EDTA \cdot 2H_2O$.

11. The composition of claim 10, wherein said $Na_4EDTA \cdot 2H_2O$ comprises from about 1% to about 25% by weight of said composition.

12. The composition of claim 11 wherein the mesh-size profile of said EDTA is a maximum of 25% through U.S.S. 100 mesh screen and 0% remaining on U.S.S. 20 mesh screen.

13. The composition of claim 10, wherein the chelating value of said $Na_4EDTA \cdot 2H_2O$ is at least about 238.

14. The composition of claim 1 wherein said proteolytic enzyme is a protease derived from *Bacillus licheniformis*.

15. The composition of claim 1 wherein said proteolytic enzymes are present in an amount from about 0.2% to about 5% by weight of said composition.

16. The composition of claim 1, wherein said monopersulfate is selected from the group consisting of alkali metal monopersulfates and alkaline earth metal monopersulfates.

17. The composition of claim 1, wherein said monopersulfate is sodium or potassium monopersulfate.

18. The composition of claim 1, wherein said anhydrous perborate is selected from the group consisting of alkali metal perborates and alkaline earth metal perborates.

19. The composition of claim 1, wherein said anhydrous perborate is potassium or sodium anhydrous perborate.

20. The composition of claim 1, wherein the weight ratio of perborate monohydrate to anhydrous perborate to polymeric fluorocarbon compound is about 54.2:45.2:0.6.

21. The composition of claim 1, wherein said perborate monohydrate is potassium or sodium perborate monohydrate.

22. The composition of claim 1, wherein the weight ratio of perborate monohydrate/monopersulfate compound is from about 3:1 to about 1:1.

23. The composition of claim 22, wherein the weight ratio of perborate monohydrate/monopersulfate compound is about 1.7:1.

24. The composition of claim 1, wherein a detergent is a component of said composition.

25. The composition of claim 24, wherein said detergent is an anionic detergent.

26. The composition of claim 25, wherein said anionic detergent is present in the amount of up to about 5% by weight of the composition.

27. A process for preparing a denture cleansing tablet according to claim 24 comprising the step of:
(a) preparing a compacted compressed mixture comprising anhydrous perborate salts and perborate monohydrate salts in combination with a lubricant and compression aid; and
(b) grinding said compacted mixture into a pregranulation mixture, or premix; and
(c) adding the pregranulation mixture, or premix, to the other materials in the denture cleansing composition and mixing; and
(d) adding detergent to the mixture and mixing for up to 3 minutes; and
(e) forming the resultant blended mixture into a cohesive tablet.

28. The process of claim 27 wherein said compacted mixture is pre-dried to a free moisture level of about 0.3% to about 1.5% by weight of the compacted mixture.

29. The process of claim 28 wherein said compacted mixture is pre-dried to a free moisture level of less than about 0.3% by weight of the compacted mixture.

* * * * *